(12) United States Patent
Toda et al.

(10) Patent No.: US 6,376,707 B1
(45) Date of Patent: Apr. 23, 2002

(54) CRYSTAL POLYMORPHISM OF AMINOETHYLPHENOXYACETIC ACID DERIVATIVE

(75) Inventors: Michio Toda; Tetsuro Tamai; Nobuyuki Tanaka, all of Nagano; Kiyoshi Kasai; Junichi Sonehara, both of Fukui; Eiji Tsuru, Nagano, all of (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/889,857

(22) PCT Filed: Jan. 17, 2000

(86) PCT No.: PCT/JP00/00168

§ 371 Date: Jul. 23, 2001

§ 102(e) Date: Jul. 23, 2001

(87) PCT Pub. No.: WO00/43350

PCT Pub. Date: Jul. 27, 2000

(30) Foreign Application Priority Data

Jan. 21, 1999  (JP) ............................................ 11-013639

(51) Int. Cl.⁷ ............................................ C07C 229/00
(52) U.S. Cl. ........................ 562/451; 562/433; 562/442
(58) Field of Search ................................. 562/433, 442, 562/451

(56) References Cited

FOREIGN PATENT DOCUMENTS

JP          WO 99/05090    * 4/1999

* cited by examiner

*Primary Examiner*—Gary Geist
*Assistant Examiner*—Hector M Reyes
(74) *Attorney, Agent, or Firm*—Sughrue Mion, PLLC

(57) ABSTRACT

The present invention relates to a crystalline polymorph of 2-[4-[2-[[(1S,2R)-2-hydroxy-2-(4-hydroxy-phenyl)-1-methylethyl]amino]ethyl]phenoxy]acetic acid having strong diffraction peaks (diffraction angle: 2θ±0.1°) at 10.8, 19.1, 19.3, 19.8, 20.6 and 27.0° in powder X-ray diffraction pattern, which has potent $\beta_2$- and $\beta_3$-adrenoceptor stimulating effects and is useful as an agent for relieving pain and promoting the removal of calculi in urolithiasis, and the like. For example, the crystalline polymorph can be prepared by hydrolyzing ethyl 2-[4-[2-[[(1S,2R)-2-hydroxy-2-(4-hydroxyphenyl)-1-methylethyl]-amino]ethyl]phenoxy] acetate phosphate by sodium hydroxide, adding an aqueous phosphoric acid solution at 40° C. and over, adding a mixed solvent of water and methanol or methanol to the resulting compound, and stirring the suspension at 40° C. to reflux temperature for 30 minutes to several hours.

1 Claim, 3 Drawing Sheets

CRYSTAL POLYMORPHISM OF AMINOETHYLPHENOXYACETIC ACID DERIVATIVE

This application is a 371 of PCT/JP00/00168, which claims priority of JP 13639.

TECHNICAL FIELD

The present invention relates to a novel crystalline polymorph of an aminoethylphenoxyacetic acid derivative which is useful as a medicament.

More particularly, the present invention relates to a crystalline polymorph (crystalline form α) of an aminoethylphenoxyacetic acid derivative represented by the formula:

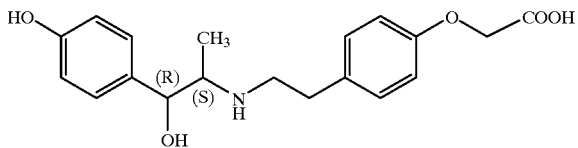

(chemical name: 2-[4-[2-[[(1S,2R)-2-hydroxy-2-(4-hydroxy-phenyl)-1-methylethyl]amino]ethyl]phenoxy] acetic acid) which has potent $\beta_2$- and $\beta_3$-adrenoceptor stimulating effects and is useful as an agent for relieving pain and promoting the removal of calculi in urolithiasis, and the like.

BACKGROUND ART

2-[4-[2-[[(1S,2R)-2-Hydroxy-2-(4-hydroxyphenyl)-1-methylethyl]amino]ethyl]phenoxy]acetic acid is a novel compound and is not disclosed in any literature. Therefore, its physical properties and pharmacological activities are not known at all.

The inventors of the present invention have investigated the properties of 2-[4-[2-[[(1S,2R)-2-hydroxy-2-(4-hydroxyphenyl)-1-methylethyl]amino]ethyl ]-phenoxy] acetic acid. It was found that it is hard to obtain this compound of uniform quality since the compound has several crystalline polymorphs and the sort and ratio vary depending upon differences in method and condition for preparing.

In a compound having crystalline polymorphs, each crystalline polymorph generally differs in various properties. Even if compounds are chemical-structurally same each other, there are cases where their effects are quite different. Especially, it is known that such compounds show different solubility, solubility rate, stability and the like in medicaments. That is, in case that same compound is used, it is considered that it can not attain desired effects depending upon difference in crystalline polymorphs. On the other hand, it is also considered that unexpected effects result in an accidental case. Accordingly, it requires to provide a compound of uniform quality so as to show continually constant effects. Therefore, when a compound having crystalline polymorphs is used as a medicament, it is requested that an established crystalline compound is stably provided to attain uniform quality and constant effects which should be required as a medicament. In addition, a stable crystalline polymorph which can keep same quality in storage is desired.

2-[4-[2-[[(1S,2R)-2-Hydroxy-2-(4-hydroxyphenyl)-1-methylethyl]amino]ethyl]phenoxy]acetic acid has several crystalline polymorphs. Some crystalline polymorphs would be mixed depending upon methods for preparing. Furthermore, it is hard to keep quality of the prepared crystalline polymorph uniform because its form would vary depending upon an external environment in storage. Thus, it is eagerly desired to find a stable crystalline polymorph of the above compound in order to keep uniform quality and constant effects which are required as a medicament and to establish a method for preparing such crystalline polymorph continually and constantly.

DISCLOSURE OF THE INVENTION

The present invention relates to a crystalline polymorph (crystalline form α) of 2-[4-[2-[[(1S,2R)-2 -hydroxy-2-(4-hydroxyphenyl)-1-methylethyl]amino]ethyl]-phenoxy] acetic acid having strong diffraction peaks (diffraction angle: $2\theta \pm 0.1°$) at 10.8, 19.1, 19.3, 19.8, 20.6 and 27.0° in powder X-ray diffraction pattern.

That is, the inventors of the present invention conducted extensive investigation of crystalline polymorphs of 2-[4-[2-[[(1S,2R)-2-hydroxy-2-(4-hydroxy-phenyl)-1-methylethyl]amino]ethyl]phenoxy]acetic acid which is useful as an agent for relieving pain and promoting the removal of calculi in urolithiasis, and the like. As a result, it was found that the crystalline polymorph of the present invention can be uniformly prepared according to the following method and that the crystalline polymorph of the present invention have an excellent low hygroscopicity and the like, and therefore is extremely useful as a medicament, thereby resulting in the accomplishment of the present invention.

For example, the crystalline polymorph of the present invention can be prepared by hydrolyzing ethyl 2-[4-[2-[[(1S,2R)-2-hydroxy-2-(4-hydroxyphenyl)-1-methyl-ethyl] amino]ethyl]phenoxy]acetate phosphate by sodium hydroxide, adding an aqueous phosphoric acid solution at 40° C. and over, collecting the resulting 2-4-[2-[[(1S,2R)-2-hydroxy-2-(4-hydroxyphenyl)-1 -methylethyl]-amino] ethyl]phenoxy]acetic acid by filtration, adding a mixed solvent of water and methanol (1:1 or more in volume) or methanol to the wet solid, and stirring the suspension at 40° C. to reflux temperature for 30 minutes to several hours. The temperature and the time of stirring can be appropriately decided depending on the volume to be treated, and the sort and volume of the solvent used.

As examples of crystalline polymorphs other than the crystalline polymorph of the present invention, there are the crystalline polymorph (crystalline form γ) having strong diffraction peaks (diffraction angle: $2\theta \pm 0.1°$) at 18.1, 19.7, 20.3, 21.2 and 22.4° and the crystalline polymorph (crystalline form 67) having strong diffraction peaks (diffraction angle: $2\theta \pm 0.1°$) at 10.2, 13.2, 17.6, 19.8 and 20.6° in powder X-ray diffraction pattern. These crystalline polymorphs easily absorb moisture to convert into their hydrates while the crystalline polymorph (crystalline form α) of the present invention does not absorb moisture even if it is allowed to stand for 10 days under relative fumidities of 51–93%. Thus, the crystalline polymorph of the present invention has an excellent low hygroscopicity and good storage. In addition, the crystalline polymorph of the present invention shows solubility of 2.7 mg/mL in water (37° C.) and has more excellent solubility than 1.8 mg/mL of the crystalline form δ. Thus, the crystalline polymorph of the present invention is favorable to oral administration and has a favorable efficiency in preparing liquid preparations such as injections. Furthermore, the crystalline polymorph of the present invention shows an excellent drug absorption when it is orally administered.

The crystalline form γ can be prepared by dissolving 2-[4-[2-[[(1S,2R)-2-hydroxy-2-(4-hydroxy-phenyl)-1-methylethyl]amino]ethyl]phenoxy]acetic acid in an aqueous sodium hydroxide solution, neutralizing the solution with hydrochloric acid under ice-cooling, collecting the resulting crystals by filtration, and drying at 40–60° C. for several hours under reduced pressure. The crystalline form δ can be prepared by dissolving 2-[4-[2-[[(1S,2R)-2-hydroxy-2-(4-hydroxy-phenyl)-1-methylethyl]amino]ethyl]phenoxy] acetic acid in water and methanol (about 7:3 in volume), concentrating the solution under reduced pressure with care to avoid high temperature, collecting the resulting crystals by filtration, and drying at 40–60° C. for about 10–20 hours under reduced pressure.

BEST MODE FOR CARRYING OUT THE INVENTION

Figure 1:
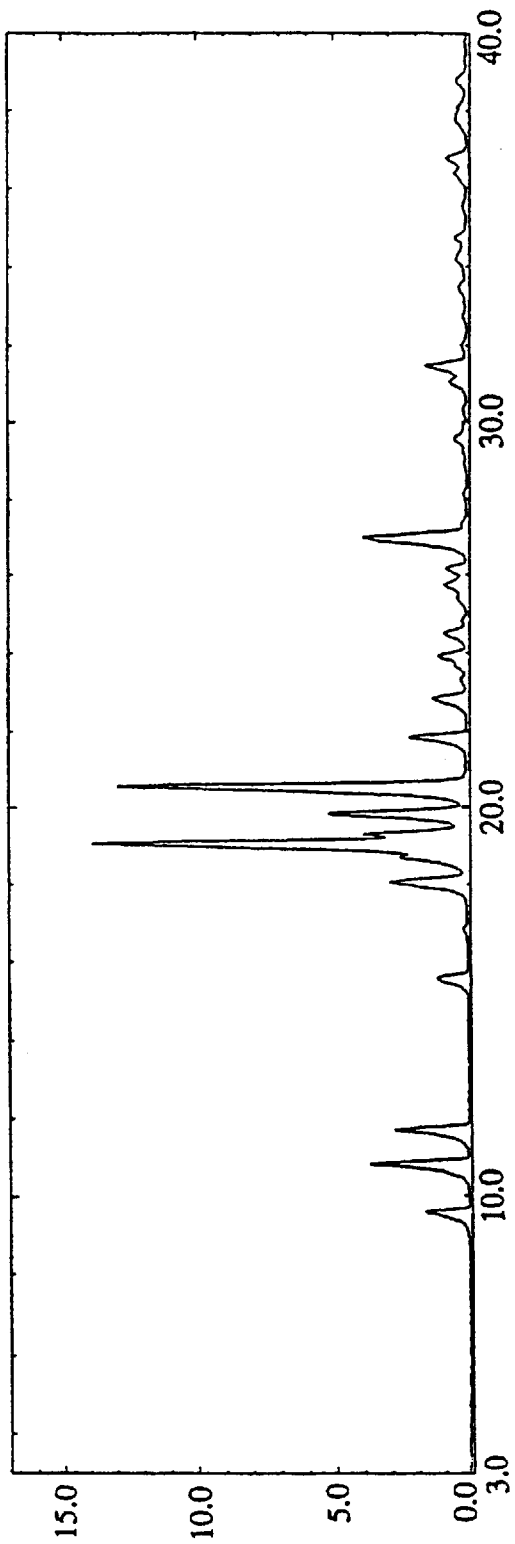
FIG. 1 is a powder X-ray diffraction pattern of the crystalline polymorph (crystalline form α) of 2-[4-[2-[[(1S,2R)-2-hydroxy-2-(4-hydroxyphenyl)-1-methylethyl]-amino]ethyl]phenoxy]acetic acid of the present invention using a monochromator. The axis of the ordinates shows diffraction intensity (kcps), and the axis of the abscissas shows diffraction angle (2θ).

The present invention is further illustrated in more detail by way of the following Reference Examples, Example, Comparative Examples and Test Examples. The melting points of various crystalline polymorphs were measured by thermogravimetric and differential thermal analyzer (TG/DTA), Thermo plus TG8120 (Rigaku) at a heating rate of 10° C./min and were expressed as extrapolated initial temperature. The powder X-ray diffraction pattern of various crystalline polymorphs were examined using CuKα-ray beam (1.541 Å) by X-ray diffraction analyzer, RINT1400 (Rigaku).

REFERENCE EXAMPLE 1

Ethyl 2-[4-(2-hydroxyethyl)phenoxy]acetate

To a solution of 4-(2-hydroxyethyl)phenol (5 g) in acetone (45 mL) was added anhydrous potassium carbonate (6.5 g) at room temperature, and the mixture was stirred for 30 minutes. Ethyl bromoacetate (4.4 mL) was added dropwise to the reaction mixture at 40–45° C. of internal temperature, and the mixture was stirred at 40° C. for 8 hours. After the insoluble materials were filtered off, the filtrate was concentrated under reduced pressure. The residue was purified by column chromatography on silica gel (eluent: hexane/ethyl acetate) to give ethyl 2-[4-(2-hydroxyethyl)phenoxy]acetate (5.8 g).

$^1$H-NMR (CDCl$_3$) δ ppm: 1.28 (3H, t, J=7.1 Hz), 2.32 (1H, br), 2.76 (2H, t, J=5.8 Hz), 3.84 (2H, m), 4.24 (2H, q, J=7.1 Hz), 4.57 (2H, s), 6.88 (2H, d, J=7.8 Hz), 7.12 (2H, d, J=7.8 Hz).

REFERENCE EXAMPLE 2

Ethyl 2-[4-(2-methanesulfonyloxyethyl)phenoxy] acetate

To a solution of ethyl 2-[4-(2-hydroxyethyl)-phenoxy] acetate (7.3 g) in ethyl acetate (22 mL) was added triethylamine (5.9 mL) at room temperature under a nitrogen atmosphere, and the mixture was stirred. Methanesulfonyl chloride (2.8 mL) was added dropwise to the mixture at 0–15° C. of internal temperature, and the mixture was stirred at room temperature for 30 minutes. After water was added to the reaction mixture, the aqueous layer was separated and extracted with ethyl acetate. The combined organic layers were washed with a saturated aqueous sodium bicarbonate solution and brine, and dried over anhydrous magnesium sulfate. After the solvent was removed under reduced pressure, ethyl acetate (8.6 mL) and 2-propanol (23 mL) were added to the residue, and the mixture was heated to dissolve. After cooling to room temperature, the resulting crystals were collected by filtration to give ethyl 2-[4-(2-methanesulfonyloxyethyl)-phenoxy]acetate (7.2 g).

$^1$H-NMR (CDCl$_3$) δ ppm: 1.29 (3H, t, J=7.1 Hz), 2.84 (3H, s), 2.99 (2H, t, J=6.9 Hz), 4.26 (2H, q, J=7.1 Hz), 4.37 (2H, t, J=6.9 Hz), 4.60 (2H, s), 6.87 (2H, d, J=8.7 Hz), 7.15 (2H, d, J=8.7 Hz).

REFERENCE EXAMPLE 3

Ethyl 2-[4-[2-[[(1S.2R)-2-hydroxy-2-(4-hydroxyphenyl)-1-methylethyl]amino]ethyl] phenoxy]acetate Phosphate A mixture of (1R,2S)-2-amino-1-(4-hydroxyphenyl)-propan-1-ol (8.8 g), ethyl 2-[4-(2-methanesulfonyloxy-ethyl)phenoxy]acetate (15.9 g), diisopropylamine (11 mL) and N,N-dimethylacetoamide (61 mL) were stirred at 75° C. for 3.5 hours under a nitrogen atmosphere. After cooling to room temperature, a mixed solvent of ethyl acetate and toluene (9/1) and water were added to the reaction mixture. The aqueous layer was separated and extracted with a mixed solvent of ethyl acetate and toluene (9/1). The combined organic layers were washed with water and 18% aqueous sodium chloride solution, and dried over anhydrous sodium sulfate. After the solvent was removed under reduced pressure, ethyl acetate (14 mL) and ethanol (92 mL) were added to the residue, and 16% phosphoric acid ethanol solution (32 g) was added dropwise to the mixture at room temperature with stirring. The resulting crystals were collected by filtration to give ethyl 2-[4-[2-[[(1S,2R)-2-hydroxy-2-(4-hydroxyphenyl)-1-methylethyl]amino]ethyl]-phenoxy]acetate phosphate (12.4 g).

$^1$H-NMR (DMSO-d$_6$) δ ppm:

0.89 (3H, d, J=6.6 Hz), 1.23 (3H, t, J=7.1 Hz), 2.80–3.15 (5H, m), 4.16 (2H, q, J=7.1 Hz), 4.73 (2H, s), 4.92 (1H, br s), 6.71 (2H, d, J=8.6 Hz), 6.85 (2H, d, J=8.6 Hz), 7.13 (2H, d, J=8.6 Hz), 7.16 (2H, d, J=8.6 Hz), 7.92 (4H, br).

EXAMPLE 1

2-[4-[2-[[(1S,2R)-2-Hydroxy-2-(4-hydroxyphenyl)-1-methyl-ethyl]amino]ethyl]phenoxy]acetic Acid (Crystalline Form α)

To ethyl 2-[4-[2-[[(1S,2R)-2-hydroxy-2-(4-hydroxyphenyl)-1-methylethyl]amino]ethyl]phenoxy]acetate phosphate (62.0 g) was added 2 mole/L aqueous sodium hydroxide solution (393 mL), and the mixture was heated to 40° C. of internal temperature with stirring to dissolve. 4 Mole/L aqueous phosphoric acid solution (115 mL) was added dropwise to the solution at 40–46° C. of internal temperature. After stirring at room temperature overnight, the resulting crystals were collected by filtration and washed with water to obtain white crystals. The resulting crystals suspended in a mixed solvent (200 mL) of water and methanol (1/8) were heated under reflux for 30 minutes. After cooling to room temperature, the crystals were collected by filtration and dried at 40–50° C. for 3 hours under reduced pressure to give 2-[4-[2-[[(1S,2R)-2-hydroxy-2-(4-hydroxyphenyl)-1-methylethyl]amino]ethyl]-phenoxy]acetic Acid (Crystalline Form α) (50.0 g). A powder X-ray diffraction pattern of the crystalline polymorph (crystalline form α) is shown in the following FIG. 1.

Melting point: 235.1° C. (decomposition); $^1$H-NMR (DMSO-$d_6$) δ ppm: 0.91 (3H, d, J=6.6 Hz), 2.55–2.75 (2H, m), 2.90–3.05 (2H, m), 3.15–3.25 (1H, m), 4.25–4.40 (2H, m), 5.00–5.10 (1H, m), 6.65–6.80 (4H, m), 6.91 (2H, d, J=8.6 Hz), 7.13 (2H, d, J=8.6 Hz), 9.40 (1H, br); Specific rotation: $[\alpha]_D^{25}$=−10.0√ (c=1.00, 1 mole/L hydrochloric acid).

Comparative Example 1

2-[4-[2-[[(1S,2R)-2-Hydroxy-2-(4-hydroxyphenyl)-1-methyl-ethyl]amino]ethyl]phenoxy]acetic Acid (Crystalline Form γ)

Figure 2:
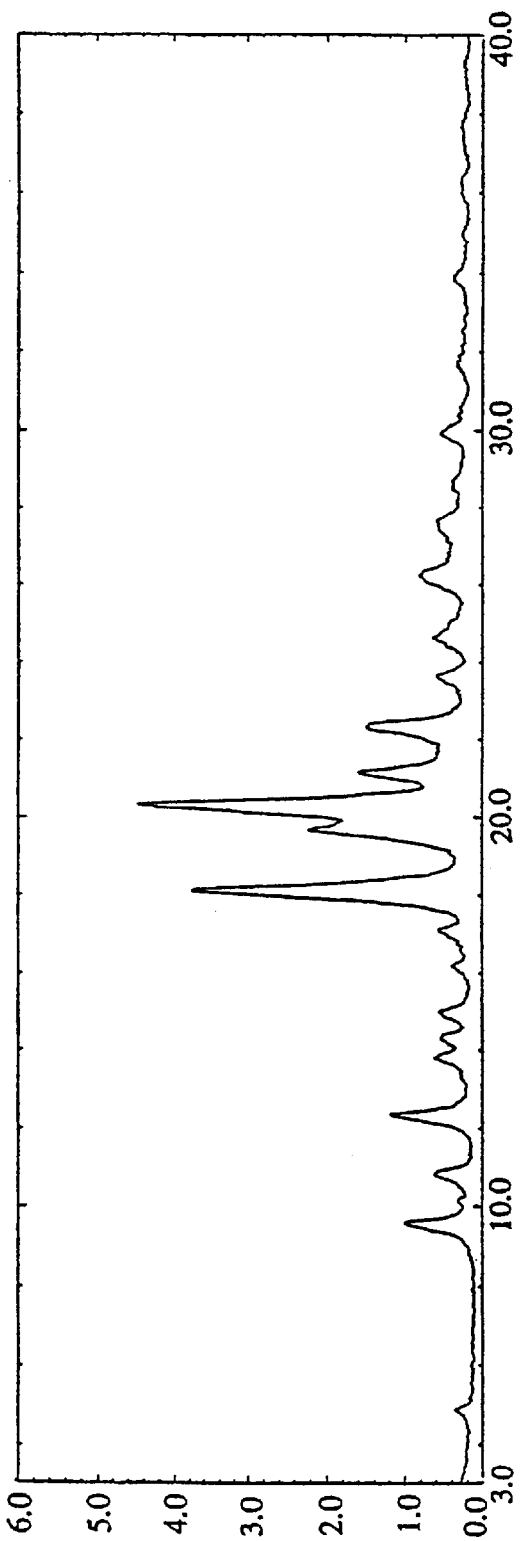
FIG. 2 is a powder X-ray diffraction pattern of a crystalline polymorph (crystalline form γ) of 2-[4-[2-[[(1S,2R)-2-hydroxy-2-(4-hydroxyphenyl)-1-methylethyl]-amino]ethyl] phenoxy]acetic acid using a monochromator. The axis of the ordinates shows diffraction intensity (kcps), and the axis of the abscissas shows diffraction angle (2θ).

2-[4-[2-((1S,2R)-2-Hydroxy-2-(4-hydroxyphenyl)-1-methylethyl]amino]ethyl]phenoxy]acetic acid (crystalline form α) (1.4 g) was dissolved in a mixed solvent of 1 mole/L aqueous sodium hydroxide solution (20 mL) and water (125 mL), and 1 mole/L hydrochloric acid (20 mL) were added to the solution under ice-cooling with stirring. After stirring for 30 minutes under ice-cooling, the resulting crystals were collected by filtration, washed with water and dried at 50° C. for 3 hours under reduced pressure to give 2-[4-[2-[[(1S,2R)-2-hydroxy-2-(4-hydroxy-phenyl)-1-methylethyl]amino]ethyl]phenoxy]acetic acid (crystalline form γ) (0.78 g). A powder X-ray diffraction pattern of the crystalline polymorph (crystalline form γ) is shown in the following FIG. 2.

Melting point: 189.8° C. (decomposition).

Comparative Example 2

2-[4-[2-[[(1S,2R)-2-Hydroxy-2-(4-hydroxyphenyl)-1-methyl-ethyl]amino]ethyl]phenoxy]acetic Acid (Crystalline Form δ)

Figure 3:
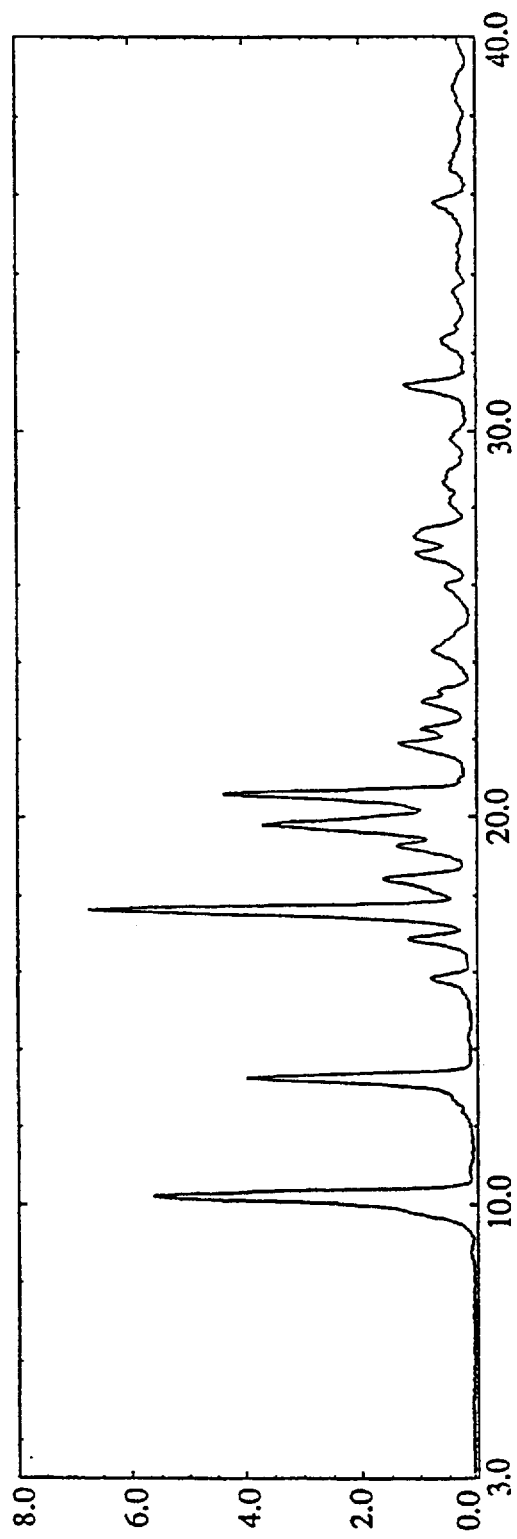
FIG. 3 is a powder X-ray diffraction pattern of a crystalline polymorph (crystalline form () of 2-[4-[2-[[(1S,2R)-2-hydroxy-2-(4-hydroxyphenyl)-1-methylethyl]-amino]ethyl] phenoxy]acetic acid using a monochromator. The axis of the ordinates shows diffraction intensity (kcps), and the axis of the abscissas shows diffraction angle (2θ).

2-[4-[2-[[(1S,2R)-2-Hydroxy-2-(4-hydroxyphenyl)-1-methylethyl]amino]ethyl]phenoxy]acetic acid (crystalline form α) (2.0 g) was dissolved in a mixed solvent of methanol (30 mL) and water (70 mL) by heating. After cooling to room temperature, the resulting insoluble materials were filtered off and the filtrate was concentrated under reduced pressure. After allowing to stand at room temperature for 30 minutes, the resulting crystals were collected by filtration and dried at 40° C. for 18 hours under reduced pressure to give 2-[4-[2-[[(1S,2R)-2-hydroxy-2-(4-hydroxyphenyl)-1-methylethyl]-amino]ethyl]phenoxy]acetic acid (crystalline form δ) (1.8 g). A powder X-ray diffraction pattern of the crystalline polymorph (crystalline form δ) is shown in the following FIG. 3.

Melting point: 236.3° C. (decomposition).

TEST EXAMPLE 1

$\beta_2$-Adrenoceptor Stimulating Effect

The uteri of pregnant SD rats (pregnancy day of 21) were isolated, and longitudinal preparations of approximately 15 mm in length and approximately 5 mm in width free from the basal plate were prepared. The experiment was conducted according to the Magnus method. The preparations with a tension of 1 g were exposed to Locke-Ringer solution maintained at 37° C. and gassed with a mixture of 95% of oxygen and 5% of carbon dioxide. Spontaneous contractions of the myometrium were isometrically measured with a force-displacement transducer and recorded by a rectigram. 2-[4-[2-[[(1S, 2R)-2-Hydroxy-2-(4-hydroxyphenyl)-1-methylethyl]amino]ethyl]-phenoxy]acetic acid was cumulatively added to the Magnus bath every 5 minutes. The drug efficacy was evaluated by comparing the sum of uterine contractions during 5 minutes after the addition of the drug with that during 5 minutes before the addition of the drug which was expressed as 100%. The 50% inhibitory drug concentration (i.e., $EC_{50}$ value) of this compound was $3.1 \times 10^{-8}$ M.

TEST EXAMPLE 2

$\beta_3$-Adrenoceptor Stimulating Effect

The ureters of male ferrets (1100–1400 g in body weight) were isolated, and longitudinal preparations of approximately 20 mm in length free from the connective tissue were prepared. The experiment was conducted according to the Magnus method. The preparations with a tension of 0.5 g were exposed to Krebs-Henseleit solution maintained at 37° C. and gassed with a mixture of 95% of oxygen and 5% of carbon dioxide. Spontaneous contractions of the ureters were isometrically measured with a force-displacement transducer and recorded by a rectigram. 2-[4-[2-[[(1S,2R)-2-Hydroxy-2-(4-hydroxyphenyl)-1-methylethyl]-amino]ethyl]phenoxy]acetic acid was cumulatively added to the Magnus bath every 3 minutes. The drug efficacy was evaluated by comparing the sum of ureter contractions during 3 minutes after the addition of the drug with that during 3 minutes before the addition of the drug which was expressed as 100%. The 50% inhibitory drug concentration (i.e., $EC_{50}$ value) of this compound was $1.4 \times 10^{-8}$ M.

What is claimed is:

1. A crystalline polymorph of 2-[4-[2-[[(1S,2R)-2-hydroxy-2-(4-hydroxyphenyl)-1-methylethyl]amino]ethyl]-phenoxy]acetic acid having strong diffraction peaks (diffraction angle: 2θ±0.10°) at 10.8, 19.1, 19.3, 19.8, 20.6 and 27.0° in powder X-ray diffraction pattern.

* * * * *

UNITED STATES PATENT AND TRADEMARK OFFICE
CERTIFICATE OF CORRECTION

PATENT NO.     : 6,376,707 B1
DATED          : April 23, 2002
INVENTOR(S)    : Michio Toda et al.

It is certified that error appears in the above-identified patent and that said Letters Patent is hereby corrected as shown below:

<u>Title page,</u>
Item [57], ABSTRACT,
Line 5, after "in" insert -- its --;
Line 12, after "phosphate", delete "by" and insert -- with --.

<u>Column 1,</u>
Line 44, delete "method and condition" and insert -- the methods and conditions --;
Line 45, after "preparing" insert -- the same --;
Line 48, after "chemical-structurally", insert -- the --, and after "same" insert -- as --;
Line 50, delete "(crystalline form 67)" and insert -- (crystalline form δ) --;
Line 52, after "in" insert -- the --, and after "that" insert -- the --;
Line 53, delete "can not" and insert -- cannot --;
Line 56, delete "requires" and insert -- is required --;
Line 59, delete "requested" and insert -- desirable --;
Line 60, delete "is";
Line 61, delete "which should";
Line 62, delete "be required as" and insert -- required in --;
Line 63, after "keep" insert -- the --.

<u>Column 2,</u>
Line 1, after "preparing" insert -- the same --;
Line 2, after "keep" insert -- the --;
Line 3, delete "would" and insert -- will --;
Line 4, delete "an" and insert -- the --;
Line 7, delete "as" and insert -- in --;
Line 17, after "in" insert -- its --;
Line 28, delete "have" and insert -- has --;
Line 50, delete "(crystalline form 67)" and insert -- (crystalline form δ) --;
Line 52, after "in" insert -- their -- and delete "pattern" and insert -- patterns --;
Line 56, delete "fumidities" and insert -- humidities --;
Line 59, after "storage" insert -- capability --.

<u>Column 3,</u>
Lines 21, 28 and 34, delete "ordinates" and insert -- ordinate --;
Lines 22, 29 and 35, delete "abscissas" and insert -- abscissa --;
Line 31, delete "form ()" and insert -- form δ --;
Line 42, delete "by" and insert -- with a --;
Line 46, delete "pattern" and insert -- patterns --;
Line 48, delete "by" and insert -- using a --.

UNITED STATES PATENT AND TRADEMARK OFFICE
CERTIFICATE OF CORRECTION

PATENT NO. : 6,376,707 B1
DATED : April 23, 2002
INVENTOR(S) : Michio Toda et al.

It is certified that error appears in the above-identified patent and that said Letters Patent is hereby corrected as shown below:

Column 4,
Line 39, delete "were" and insert -- was --.

Column 5,
Line 20, delete "$[\alpha]_D^{25} = -10.0\sqrt{}$" and insert -- $[\alpha]_D^{25} = -10.0°$ --;
Line 33, delete "were" and insert -- was --.

Column 6,
Line 56, delete "$2\theta \pm 0.10°$" and insert -- $2\theta \pm 0.1°$ --.

Signed and Sealed this

Sixth Day of June, 2006

JON W. DUDAS
*Director of the United States Patent and Trademark Office*